United States Patent [19]

Lüssling et al.

[11] 4,136,108

[45] Jan. 23, 1979

[54] PROCESS FOR THE PRODUCTION OF MALONONITRILE

[75] Inventors: Theodor Lüssling; Ferdinand Theissen, both of Gross-Auheim; Wolfgang Weigert, Offenbach, all of Germany

[73] Assignee: Deutsche Gold- und Silber-Scheideanstalt vormals Roessler, Frankfurt, Germany

[21] Appl. No.: 294,925

[22] Filed: Oct. 4, 1972

Related U.S. Application Data

[62] Division of Ser. No. 812,308, Apr. 1, 1969, Pat. No. 3,729,499.

[30] Foreign Application Priority Data

Apr. 5, 1968 [DE] Fed. Rep. of Germany ....... 1768154
Mar. 5, 1969 [DE] Fed. Rep. of Germany ....... 1911174

[51] Int. Cl.² .................. C07C 121/22; C07C 120/00
[52] U.S. Cl. ............................................... 260/465.8 R
[58] Field of Search ................................. 260/465.8 R

[56] References Cited

U.S. PATENT DOCUMENTS 3,655,721  4/1972  Arni et al. ..................... 260/465.8 R Primary Examiner—Joseph Paul Brust
Attorney, Agent, or Firm—Cushman, Darby & Cushman

[57] ABSTRACT

Malononitrile is prepared by the short time high temperature reaction of gaseous acetonitrile and cyanogen chloride in the molar ratio of acetonitrile to cyanogen halide of above 1 characterized in that the well mixed reaction components are reacted at an average temperature below 800° C. and the reaction is quenched to condense acetonitrile and malononitrile by introducing a cooling medium into the reaction system.

10 Claims, No Drawings

PROCESS FOR THE PRODUCTION OF MALONONITRILE

This application is a division of application Ser. No. 812,308, filed Apr. 1, 1969, now U.S. Pat. No. 3,729,499.

Dixon U.S. Pat. No. 2,553,406 discloses the production of a malonitrile by the reaction of a cyanogen halide with an aliphatic mononitrile at 600°–700° C. for 0.5 second or more preferably for 5 to 15 seconds. To make malononitrile itself acetonitrile is employed as the aliphatic mononitrile. In the Dixon procedure a molecular proportion of mononitrile to cyanogen halide of greater than 1 is used but the yield amounts to only about 18%. Dixon U.S. Pat. No. 2,606,917 shows that introduction of inert gases such as nitrogen, carbon dioxide or steam during the reaction does not improve the yield, since a yield of only 16.5% malononitrile is obtained in experiment 7.

Further it has been disclosed in published Japanese patent application 41(1966)-16506 that malononitrile can be produced from acetonitrile and cyanogen chloride with catalytic amounts of chlorine at 700°–900° C. in the presence of inert gases. The addition of the chlorine to the cyanogen chloride should amount to 50% chlorine by weight. The yield determined only by gas chromotography amounted to about 70% based on the added cyanogen chloride.

By maintenance of the Japanese process it has been proven, however, that the yield of the isolated substance was essentially less than the yields given by gas chromatography and is 30 to 60%. Through the presence of the chlorine at the high temperature the aliphatic mononitrile becomes intermediately chlorinated and decomposes into hydrogen chloride and unknown decomposition products. These nitrile losses can amount to up to 70% of the added mononitrile. Additionally chlorine has a known corrosive effect on the apparatus so that only special materials can be used for the apparatus.

It is the object of the present invention to obtain malononitrile through the reaction of cyanogen halide with acetonitrile with essentially higher yields of the malononitrile and almost quantitative recovery of the unreacted mononitrile.

It has now been found that malononitrile can be produced in increased yields without use of a catalyst if gaseous anhydrous or aqueous acetonitrile and gaseous cyanogen halide in the proportion of over 1 mole of acetonitrile per mole of cyanogen halide are brought into contact with each other for a short period of time at an average reaction temperature below 800° C., if necessary in the presence of inert gases, and the reaction mixture is chilled by introduction of a cooling medium whereby in the presence of water in the reaction system the reaction mixture is neutralized during the condensation by the addition of acid binding materials.

Acetonitrile is added either in anhydrous form or containing water. Thus it can contain up to 50% by weight of water. As cyanogen halides there can be employed cyanogen chloride and cyanogen bromide. Cyanogen chloride is preferred.

The gaseous reaction partners are added in well mixed condition, e.g. through the use of known turbulent mixing processes.

The most favorable residence time is between 1 to 15 seconds, preferably 5 to 8 seconds, the most favorable average temperature is between 700° and 780° C. and the most favorable molar proportions of acetonitrile to cyanogen chloride are from 2:1 to 10:1. The reaction is generally carried out at atmospheric pressure. The lowest average temperature is 550° C.

As inert gases there can be added nitrogen, carbon dioxide or steam. The inert gas, when employed, is added in an amount of 0.2% to 70% of the total volume of gases. Steam is especially important since in this case the inert gases are condensible and the losses of unchanged addition products and the arising final product are essentially reduced. Further in the presence of steam a definite increase in yield is noted, based on the reacted cyanogen chloride and based on the reacted acetonitrile.

The gases leaving the reaction can be chilled by any cooling means which either does not introduce impurities into the end product or which can be easily removed from it. Thus there can be used the condensing malononitrile itself, or also water or acetonitrile. Also there can be used as the cooling means acetonitrile containing up to 50% water by weight. The cooling means can be introduced into the reaction mixture in known manner, advantageously by injection. The cooling medium quenches the product quickly to below 75° C.

The water introduced as addition product inert gas or cooling means during the course of the reaction forms aqueous hydrochloric acid from the hydrogen chloride arising from the reaction. This can saponify the malononitrile produced. For this reason the reaction mixture during the cooling is simultaneously neutralized. As neutralization means there are preferably used substances which in the reaction with hydrochloric acid, form chlorides having drying properties. Especially suitable are alkali or alkali earth metal carbonates or bicarbonates, most preferably lithium, magnesium and calcium. These can be added alone or in admixture. If the chlorides formed which act as driers there is obtained a practically water free reaction product. Specific examples of suitable additives include lithium carbonate, lithium bicarbonate, sodium carbonate, sodium bicarbonate, potassium carbonate, potassium bicarbonate, magnesium carbonate, calcium carbonate, strontium carbonate and barium carbonate. Less preferably there can be used alkali metal and alkaline earth metal hydroxide and oxides such as lithium hydroxide, sodium hydroxide, potassium hydroxide, calcium hydroxide, magnesium hydroxide, barium hydroxide, lithium oxide, sodium oxide, potassium oxide, magnesium oxide, calcium oxide and barium oxide. Neutralization need only be to a pH of 0 to about 2. Mixtures of neutralizing agents can be employed.

The formation of such chloride is always very suitable if the content of water or steam amounts to 10 to 30% by weight of the acetonitrile at a molar ratio of acetonitrile to cyanogen chloride of from 8:1 to 2:1. The cooled and with the use of water neutralized mixture is distilled in the customary way. The yields of product amounts to 67.0 to 82.5% based on the reacted cyanogen chloride and up to 83% based on the reacted acetonitriles.

The technical improvement of the process of the invention primarily lies in a substantial increase in the yield of material without additional technically employed precautions.

It has further been found that an increase in yield occurs in reference to the added acetonitrile if the condensation of the reaction mixture takes place immediately inside the reactor outlet that is if the cooling means for the quenching also is introduced immediately into the reactor outlet. If aqueous solutions are added as quenching means or if steam is in the system, e.g. by addition of water containing acetonitrile then the formed hydrogen chloride must be neutralized immediately after the introduction of the condensation means. In this regard by neutralization a pH of 0 to about 2 is meant. Higher pH values are not necessary if the layers built by the condensation and neutralization are immediately separated.

A phase separation is always possible if a salt solution concentrated as high as feasible is present after the neutralization as a result of reaction of the neutralization agent and the hydrogen chloride.

The neutralization agent is preferably added as a solid. The amount of water in the system should therefore preferably be so added that after the neutralization concentrated salt solutions result, in order that the separation is made easier. By the continuous carrying out of the process, if necessary, fresh water is added corresponding to the amount of salt formed and a corresponding amount of aqueous salt solution is removed. This salt solution is distilled to recover the acetonitrile dissolved therein. In place of fresh water partially aqueous crude acetonitrile can be added as it is produced in other chemical processes. The acetonitrile then resulting from the working up of the reaction product serves without further purification as the starting material for the malononitrile synthesis. The impurities introduced into the crude malononitrile through the crude acetonitrile anyhow are separated by the necessary purification of the nitrile without additional difficulty. It further appears that a very thorough mixing of the starting products is essential as well as a removal of the coating arising through cracking on the reactor outlet.

Unless otherwise indicated all parts and percentages are by weight.

EXAMPLE 1

Gaseous acetonitrile and cyanogen chloride were brought to reaction in the presence of nitrogen in a ceramic reactor at an average temperature of about 750° C. and a maximum temperature of 820° C. in the reaction mixture, after the gases had previously been intimately mixed. The gases were added in the molar proportions of acetonitrile to cyanogen chloride to nitrogen of 5.1:1:2.1. The gaseous mixture was in the reaction zone for 6.9 seconds. The reaction product was then introduced into ice water cooled acetonitrile and finally fractionally distilled in a vacuum. There were employed 0.1 parts of the ice water cooled acetonitrile for each part of cyanogen chloride in the initial mixture. Through the distillation malononitrile was isolated as a water white product in a 66.6% yield based on the reacted cyanogen chloride and a 30% yield based on the reacted acetonitrile.

EXAMPLE 2

In the same reactor as in Example 1 a well homogenized mixture of acetonitrile, cyanogen chloride and steam were reacted at an average temperature of 773° C. and a maximum temperature of 825° C. The amount of water was 15% based on the weight of the acetonitrile. The acetonitrile and cyanogen chloride were in the molar proportions of 5.54:1. The residence time of the gaseous mixture in the reaction zone was 6.9 seconds. The product gases leaving the reactor were neutralized during the condensation with pieces of marble. There were used 2.35 parts of marble per part of cyanogen chloride. The reaction mixture was worked in the manner described in Example 1. The yield of water white malononitrile amounted to 71.6% based on the cyanogen chloride reacted and 60.1% based on the acetonitrile reacted.

EXAMPLE 3

The process of Example 2 was employed using acetonitrile and cyanogen chloride in the molar proportions of 5.75:1. The acetonitrile contained 27.2% water. The residence time was 6.8 seconds. The yield of malonitrile was 67.0% based on the cyanogen chloride reacted and 63% based on the acetonitrile reacted.

EXAMPLE 4

In the same reactor as in Example 1 acetonitrile containing 15% water was reacted with cyanogen chloride at an average temperature of 770° C. and a maximum temperature 820° C. and a residence time of the gas mixture in the reaction zone of 6.54 seconds. The molar proportions of acetonitrile to cyanogen chloride were 3.92:1. The gases leaving the reactor were condensed by injecting aqueous acetonitrile having a temperature of 20° C. and simultaneously neutralized with calcium carbonate. There were employed 152 parts of water and 2399 parts of acetonitrile in the cooling mixture and 235 parts of calcium carbonate as the neutralizing agent. The yield of water white malononitrile amounted to 74.5% based on the cyanogen chloride reacted and 57.2% based on the acetonitrile reacted.

EXAMPLE 5

In the same reactor as Example 1 anhydrous acetonitrile was reacted with cyanogen chloride in the molar proportions of 4.2:1 at an average temperature of 780° C. and a maximum temperature of 820° C. and a residence time of the gases in the reaction zone of 7.8 seconds. The gases leaving the reactor were simultaneously neutralized with 2.59 parts of calcium carbonate per part of cyanogen chloride employed and condensed through injection of aqueous acetonitrile having a temperature of 20° C. and containing 0.94 parts of water and 13.3 parts of acetonitrile per part of cyanogen chloride employed. The yield of water white malonitrile amounted to 80,1%, based on the cyanogen chloride reacted and 65% based on the acetonitrile reacted.

EXAMPLE 6

In the same reactor as Example 1 anhydrous acetonitrile was reacted with cyanogen chloride in the molar proportions of 4.45:1 at an average temperature of 776° C. and a maximum temperature of 820° C. and a residence time of the gases in the reaction zone of 7.7 seconds. The gas leaving the reactor were condensed by injecting 16.5 parts of acetonitrile based on the starting cyanogen chloride. The following fractional distillation resulted in a malononitrile yield of 77% based on the cyanogen chloride reacted.

EXAMPLE 7

In the same reactor as Example 1 anhydrous acetonitrile was reacted with cyanogen chloride in the molar proportions of 6.78:1 at an average temperature of 780° C. and a maximum temperature of 820° C. and a residence time of 8.04 seconds. The gases leaving the reactor were condensed through 1000–1400 parts of circulating water based on the cyanogen chloride employed at a temperature of 20°–30° C. and simultaneously neutralized with 2.8 parts of calcium carbonate based on the starting cyanogen chloride. The water contained acetonitrile and the reaction product corresponding to their solubility. After working up in the manner of Example 1 malononitrile was isolated as a water white product in a yield of 80.5% based on the cyanogen chloride reacted and a yield of 64.3% based on the acetonitrile reacted.

EXAMPLE 8

In the same reactor as Example 1 acetonitrile containing 15% water was reacted with cyanogen chloride in the molar proportions of 2.12:1 at an average temperature of 780° C. and a maximum temperature of 820° C. and a residence time of 6.25 seconds. The gases leaving the reactor were quenched by injection of aqueous acetonitrile containing 0.87 parts water and 10 parts acetonitrile based on the cyanogen chloride employed and were simultaneously neutralized with 2.1 parts of calcium carbonate based on the cyanogen chloride employed. The customary working up gave a yield of 66.2% water white malononitrile based on the cyanogen chloride reacted and 65.0% based on the acetonitrile reacted.

EXAMPLE 9

In the same reactor as Example 1 acetonitrile and cyanogen chloride were reacted in the molar proportions of 3.9:1 at an average reaction temperature of 775° C. and a residence time of 7.3 seconds. The acetonitrile, containing as primary impurities 3.91% hydrogen cyanide and 3.43% water, consisted of recycled acetonitrile which was obtained as low boiling fraktion ($bp_{200}$ lower than 40° C.) during the work up of the reaction products and which had been dried partially with calcium chloride. For reacted acetonitrile aqueous crude acetonitrile was supplied by introducing it into the quenching system. The reaction gases leaving the reactor were quenched in the reactor outlet through the injection of the circulating aqueous phase at a temperature of 20°–30° C. and in an amount of 1000–1400 parts per part of cyanogen chloride employed, and at the same time neutralized with calcium carbonate to a pH of 0.5. The aqueous phase formed on account of the salting out effect of the calcium chloride which arose from the neutralization of hydrochloric acid with calcium carbonate. After working up to organic phase in a vacuum and recovery of the acetonitrile dissolved in the salt containing water malononitrile was recovered in a yield of 82.5% based on the cyanogen chloride reacted and in a yield of 83% based on the acetonitrile reacted.

In the process of the present invention the unreacted acetonitrile after separation from malononitrile is recycled for reaction with cyanogen chloride.

What is claimed is:

1. A process for the production of malonic acid dinitrile which comprises reacting a reaction admixture consisting of acetonitrile and cyanogen chloride in the gaseous phase at a temperature between 740° and 780° C., said reaction admixture having a residence time of 1 to 15 seconds, and said cyanogen chloride and said acetonitrile being present in said reaction admixture in a molar ratio of 1:1 to 1:5.

2. The process according to claim 1 wherein said reaction is conducted at a temperature between 750° and 760° C.

3. A process for the production of malonic acid dinitrile which comprises reacting a reaction admixture consisting of acetonitrile and cyanogen chloride in the gaseous phase at a temperature between 740° and 780° C., said reaction admixture having a residence time of 1 to 15 seconds, and said cyanogen chloride and said acetonitrile being present in said reaction admixture in a molar ratio of 1:2 to 1:5.

4. The process according to claim 3 wherein said reaction is conducted at a temperature between 750° and 760° C.

5. A process for the production of malonic acid dinitrile which comprises reacting a reaction admixture consisting of acetonitrile and cyanogen chloride in the gaseous phase at a temperature between 750° and 780° C., said reaction admixture having a residence time of 1 to 15 seconds, and said cyanogen chloride and said acetonitrile being present in said reaction admixture in a molar ratio of 1:2 to 1:5.

6. The process according to claim 5 wherein said reaction is conducted at a temperature of 750° C.

7. A process for the production of malonic acid dinitrile which comprises reacting a reaction admixture consisting of acetonitrile and cyanogen chloride in the gaseous phase at an average temperature between 750° and 780° C., said reaction admixture having a residence time of 1 to 15 seconds, and said cyanogen chloride and said acetonitrile being present in said reaction admixture in a molar ratio of 1:1 to 1:5.

8. The process according to claim 7 wherein said reaction is conducted at an average temperature of 750° C.

9. A process for the production of malonic acid dinitrile which comprises reacting an intimate reaction admixture consisting of acetonitrile and cyanogen chloride in the gaseous phase at a temperature between 750° and 780° C., said reaction admixture having a residence time of 1 to 15 seconds, and said cyanogen chloride and said acetonitrile being present in said reaction admixture in a molar ratio of 1:2 to 1:5.1.

10. The process according to claim 9 wherein said reaction is conducted at a temperature of 750° C.

* * * * *